United States Patent [19]
Berners-Price et al.

[11] Patent Number: 5,037,812
[45] Date of Patent: Aug. 6, 1991

[54] TUMOR CELL GROWTH-INHIBITING PHARMACEUTICAL COMPOSITIONS CONTAINING PHOSPHINO-HYDROCARBON-GOLD, SILVER OR COPPER COMPLEXES

[75] Inventors: Susan J. Berners-Price, South Croydon, United Kingdom; Randall K. Johnson, Ardmore; Christopher K. Mirabelli, Exton, both of Pa.; Peter J. Sadler, Harrow Weald, United Kingdom

[73] Assignee: SmithKline Beckman Corporation, Philadelphia, Pa.

[21] Appl. No.: 873,016

[22] Filed: Jun. 11, 1986

Related U.S. Application Data

[63] Continuation-in-part of Ser. No. 718,904, Apr. 2, 1985, abandoned, which is a continuation-in-part of Ser. No. 616,621, Jun. 4, 1984, abandoned.

[51] Int. Cl.$^5$ .................... A01N 57/00; A61K 31/66
[52] U.S. Cl. .................... 514/105; 514/102; 514/107; 514/108; 516/18
[58] Field of Search .................. 556/18; 514/102, 107, 514/108, 105

[56] References Cited

U.S. PATENT DOCUMENTS 3,657,298  4/1972  King et al. ............................ 556/18
4,766,226  8/1988  Hill et al. ............................ 556/18

FOREIGN PATENT DOCUMENTS

0151046A3  4/1985  European Pat. Off. .
0164970A2  7/1985  European Pat. Off. .

OTHER PUBLICATIONS

Dines, Inorg. Chem., 11(12), 2949-52 (1972).
Cariati et al., Inor. Chim. Acta, 1(2), 315-18 (1967).
McAuliffe, J.C.S. Dalton, 1730-1735 (1979).
Bates et al., Inorg. Chim. Acta, 81(2), 151-156 (1984).
Berners-Price et al., J. Chem. Soc. Dalton Trans., 969-974 (1984).
Cariati et al., Chim. Ind. (Milan), 52(10), 995-998 (1970).
Kuhn et al., Chemiker-Zeitung, 105(3), 87-88 (1981).
Camus et al., Trans. Met. Chem., 1, 205-206 (1976).
Gaughan et al., Inorg. Chem., 10(12), 2776-2781 (1971).
Anderson et al., Can. J. Chem., 49(5), 761-6 (1971).
Leoni et al., J.C.S. Chem. Comm., 5, 240-241 (1983).
Marsich, et al., J. Inorg. Nucl. Chem., 34(3), 933-46 (1972).
Albano, J. Chem. Soc., Dalton Trans., 1938-43 (1972).
Edwards et al., J. Chem. Soc., Dalton Trans., 637-43 (1975).
Struck et al., J. Med. Chem., 9, 414-416 (1966).
Shaw et al., Inorganica Chimica Acta, 123, 213-216 (1986).
Eggleston et al., Inorganica Chimica Acta, 108, 221-226 (1985).
Mirabelli et al., Biochemical Pharmacology, 35(9), 1435-1443 (1986).
Mirabelli et al., Biochemical Pharmacology, 35(9), 1427-1433 (1986).
Mirabelli et al., J. Med. Chem., 29(2), 218-223 (1986).
Mirabelli et al., Cancer Research, 45, 32-39 (1985).
Hill et al., in an abstract (#204) from the 20th Great Lakes Regional Meeting of the American Chemical Society at Marquette Univ. on Jun. 2-4, 1986.
Berners-Price et al., in an abstract (#244) from the 20th Great Lakes Regional Mtg. of the Amer. Chem. Soc. at Marquette Univ. on Jun. 2-4, 1986.
Johnson et al., Abstract #1001, Proceedings of AACR, 26, Mar. 1985.
Snyder et al., Abstract #1007, Proceedings of AACR, 26, Mar. 1985.
Mirabelli et al., Abstract #1008, Proceedings of AACR, 26, Mar. 1985.
Mirabelli et al., Abstract #1114, Proceedings of AACR, 27, Mar. 1986.
Johnson et al., Abstract #1115, Proceedings of AACR, 27, Mar. 1986.
Mirabelli et al., Abstract #1445, AACR Abstracts, 1984, Mar. 1984.
Hill et al., Abstract #14, 190th American Chemical Society National Meeting, Chicago, Ill., Sep. 8-13, 1985.
Berners-Price et al., Inorg. Chem., 25, 3822-3827 (1986) (Oct.).
Weinstock et al., Journal of Medicinal Chemistry, 17, 139 (1974).

Primary Examiner—Paul F. Shaver
Attorney, Agent, or Firm—Carol G. Canter; Stephen Venetianer; Edward T. Lentz

[57] ABSTRACT

Pharmaceutical compositions and a method for inhibiting the growth of tumor cells by administering a tumor cell growth-inhibiting amount of a bis[bis (diphenylphosphino)hydrocarbon]-, bis[bis(diethylphsophino) hydrocarbon]-, bis[bis(diphenylphosphine-deithylphosphino) hydrocarbon]gold(I), silver(I) or copper(I) complex or a tris[bis(diphenylphosphino)ethane] dicopper(I) complex to an animal afflicted with said tumor cells.

65 Claims, No Drawings

TUMOR CELL GROWTH-INHIBITING PHARMACEUTICAL COMPOSITIONS CONTAINING PHOSPHINO-HYDROCARBON-GOLD, SILVER OR COPPER COMPLEXES

CROSS-REFERENCE TO RELATED APPLICATIONS

This application is a continuation-in-part of Ser. No. 718,904 filed Apr. 2, 1985 which is now abandoned and, which is a continuation-in-part of Ser. No. 616,621 filed June 4, 1984 which is abandoned.

BACKGROUND OF THE INVENTION

This invention relates to novel bis[bis (diphenylphosphino)hydrocarbon]-, bis[bis(diethylphosphino)hydrocarbon]-, bis[diphenylphosphino-diethylphosphino)-hydrocarbon]gold(I), silver(I) or copper(I) complexes or tris[bis(diphenylphosphino)ethane]dicopper (I) derivatives which have tumor cell growth-inhibiting activity, novel pharmaceutical compositions containing tumor cell growth-inhibiting amounts of such complexes, and a method for treating tumor cells sensitive to such complexes by administering tumor cell growth-inhibiting amounts of such complexes to a host animal afflicted by such tumor cells. As disclosed more fully below, the active ingredients are cytotoxic to mammalian cells in vitro, for example B16 melanoma cells, and tumoricidal against animal tumor cells in vivo, for example P388 leukemia and M5076 reticulum cell sarcoma in mice.

Dines, *Inorg. Chem.*, 11(12), 2949–52 (1972), discloses bis[1,2-bis(diphenylphosphino)ethane]copper(I) trifluoroacetate. Cariati et al., *Inorg. Chim. Acta*, 1(2), 315–18 (1967) disclose bis[1,2-bis(diphenylphosphino)ethane]gold(I) chloride. Bates et al., *Inorg. Chim. Acta*, 81(2), 151–156 (1984) disclose the crystal and molecular structure of bis[1,2-bis(diphenylphosphino)ethane]-gold(I) chloride. Sadler et al., *J. Chem. Soc., Dalton Trans.*, 969–974 (1984), discloses the X-ray crystal structure of bis[1,2-bis(diphenylphosphino)ethane]gold(I) hexafluoroantimonate-acetone solvate. Cariati et al., *Chim. Ind. (Milan)*, 52(10, 995–998 (1970), disclose bis[1,2-bis(diphenylphosphino)ethane]gold(I) thiocyanate. Kuhn et al., *Chemiker-Zeitung*, 105(3), 87–88 (1981), discloses bis[1,2-bis(diphenylphosphino)ethane]-silver(I) methanesulfonate. Carty et al., *Can. J. Chem.*, 49, 761–6 (1971), disclose bis[1,2-bis(diphenylphosphino)ethane]copper(I) nitrate. Leoni et al., *J.C.S. Chem. Comm.*, 5, 240–241 (1983), disclose bis[1,2-bis(diphenylphosphino)ethane]copper(I) di[copper(mesityl)]. Marsich, et al., *J. Inorg. Nucl. Chem.*, 34(3), 933–46 (1972), disclose dichlorotris-[1,2-bis(diphenylphosphino)ethane]dicopper (I)-bis-chloroform and its bromo and iodo analogs. Albano, *J. Chem. Soc., Dalton Trans*, 1938–43 (1972), discloses dichlorotris-[1,2-bis(diphenylphosphino)ethane]dicopper(I) bis-acetone. Edwards et al., *J. Chem. Soc., Dalton Trans*, 637–43 (1975), disclose bis(acetato)tris[1,2-bis(diphenylphosphino)ethane]-dicopper(I). Carty et al., *Can. J. Chem.*, 49(5), 761–6 (1971), disclose bis(nitrato) tris[1,2-bis(diphenylphosphino)ethane]dicopper(I). Struck et al., *J. Med. Chem.*, 9, 414–416 (1966), disclose cytotoxic activity for 1,2-bis(diphenyl- phosphino)ethane which is used as a starting material to prepare some of the active ingredients of the pharmaceutical compositions and methods of treatment of the subject invention. None of the aforementioned references disclose or suggest the pharmaceutical compositions or methods of treatment of the instant invention.

SUMMARY OF THE INVENTION

This invention relates to a compound of the formula:

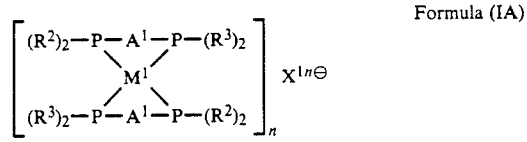

Formula (IA)

wherein $R^2$ and $R^3$ are the same and are phenyl, ethyl or monosubstituted phenyl wherein said substituent is halo, or $R^2$ is ethyl when $R^3$ is phenyl;

$A^1$ is the same and is $(CH_2)_m$ or cis—CH=CH;

m is 2 or 3;

$X^1$ is a pharmaceutically acceptable counterion;

n is equal to the negative charge of the counterion; and $M^1$ is Au(I), Ag(I) or Cu(I); provided that (a) when $M^1$ is Cu(I), $R^2$ and $R^3$ are the phenyl, and $A^1$ is $(CH_2)_2$, $X^1$ is other same and are phenyl, and $A^1$ is $(CH_2)_2$, $X^1$ is other than halo or other than nitrato;

(b) when $R^2$ and $R^3$ are the same and are ethyl, $A^1$ is $(CH_2)_2$ and $M^1$ is Au(I), $X^1$ is other than halo; and $R^2$ and $R^3$ are the same and are phenyl, $A^1$ is $(CH_2)_2$ and $M^1$ is Au(I), $X^1$ is other than chloro.

This invention also relates to a pharmaceutical composition which comprises an effective, tumor cell growth-inhibiting amount of an active ingredient and an inert, pharmaceutically acceptable carrier or diluent, wherein said composition is useful for inhibiting the growth of animal tumor cells sensitive to the active ingredient, and wherein the active ingredient is a compound of Formula (I) or Formula (II):

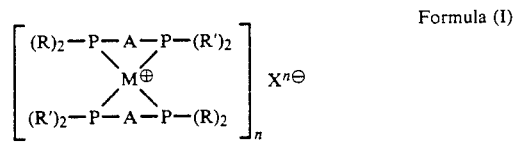

Formula (I)

wherein

R and R' are the same and are phenyl, ethyl or monosubstituted phenyl wherein said substituent is halo, or R' is ethyl when R is phenyl;

A is the same and is $(CH_2)_m$ or cis—CH=CH;

m is 2 or 3;

X is a pharmaceutically acceptable counterion;

n is equal to the negative charge of the counterion; and

M is Au(I), Ag(I) or Cu(I); provided that (a) when M is Cu(I), R and R' are the same and are phenyl, and A is $(CH_2)_{2'}$, X is other than halo; and (b) when R and R' are the same and are ethyl, A is $(CH_2)_2$, and M is Au(I), X is other than halo;

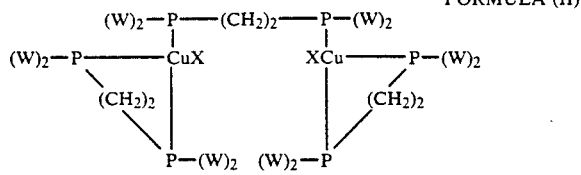

FORMULA (II)

wherein

W is the same and is phenyl; and

X is the same and is halo or nitrato.

This invention also relates to a method of inhibiting the growth of animal tumor cells sensitive to a compound of Formula (I) or Formula (II) which comprises administering to an animal afflicted with said tumor cells, an effective, tumor cell growth-inhibiting amount of a compound of Formula (I) or Formula (II).

DETAILED DESCRIPTION OF THE INVENTION

By the term "pharmaceutically acceptable counterion" is meant any counterion which has minimal or benign toxicity. Preferred counterions are those available in pharmaceutical or food grade. The pharmaceutical acceptability of a particular counterion can be determined by conventional techniques for determining toxicology. Preferred pharmaceutically acceptable counterions include monocarboxylates (e.g. formate, acetate, lactate, hippurate, amino acids), diand tri-carboxylates (e.g. malonate, citrate), phosphate and phosphate esters, phospholipids, sulphate, carbonate and bicarbonate. Especially preferred counterions include halo, nitrato, $PF_6$, methanesulfonate, 2-hydroxypropanoate, glucuronate, sulfate, cyanate, citrate, trifluoromethane-sulfonate, 2-oxopropanoate, 4-hydroxybutanoate, hydroxyacetate, 2-hydroxybutanoate, 2,3-dihydroxypropanoate, and 2-hydroxyethyl sulfonate (isethionate). 2-hydroxypropanoate (lactate), 2-oxopropanoate, hydroxyacetate, and 2,3-dihydroxypropanoate are most preferred.

One skilled in the art will recognize that all the compounds of Formula (IA) are embraced within the scope of Formula (I).

All the compounds of Formula (I) and Formula (II) can be prepared by methods available to one skilled in this art.

Unless otherwise indicated, all the starting materials necessary to prepare the compounds of Formula (I) and Formula (II) are available from commercial sources.

Generally, to prepare the gold complexes of Formula (I) where X is chloro and R and R' are the same and are phenyl or ethyl, or R is ethyl provided R' is phenyl, the starting materials are the corresponding [α, ω-bis(diphenylphosphino or diethylphosphino) or α,ω-(diethylphosphino)-α,ω-(diphenylphosphino)hydrocarbon{bis[chlorogold(I)]} complexes represented by the following general structural formula:

$(R'')_2-P-A-P-(R''')_2$  FORMULA III
    |       |
    MCl    MCl

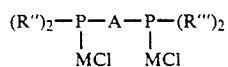

in which A is as defined above, M is Au(I), and R" and R''' are the same and are phenyl or ethyl, or R" is ethyl provided that R''' is phenyl. The gold complex of Formula (III) is reacted with the appropriate bis(α,ω-diphenylphosphino or diethylphosphino) or (diethylphosphino-diphenylphosphino)hydrocarbon compound of Formula (IV), $(R'')_2-P-A-P-(R''')_2$  FORMULA (IV)

in which A, R" and R''' are as defined above. For example, the solid metal complex of Formula (III) is added to a solution of the hydrocarbon compound of Formula (IV) in a nonreactive organic solvent, such as acetone, and the mixture maintained at room temperature for 1-2 hours.

The gold complexes of Formula (III) are prepared by reaction of 1 mole equivalent of a hydrocarbon compound of Formula (IV) with 2 mole equivalents of a reduced form of chloroauric acid hydrate obtained by treatment with thiodiglycol. The necessary Formula (IV) compounds are available from commercial sources, for example, from Strem Chemicals, Inc., Danvers, Mass.

Alternatively, the gold complexes of Formula (I) where X is chloro and R and R' are the same and are phenyl or ethyl, or R is ethyl provided that R' is phenyl, are prepared directly by reaction of 2 mole equivalents of a hydrocarbon compound of Formula (IV) with 1 mole equivalent of a reduced form of chloroauric acid hydrate obtained by treatment with thiodiglycol.

To prepare the gold complexes of Formula (I) where X is chloro and R and R' are the same and are monohalosubstituted phenyl, the starting materials are the corresponding (α,ω-bis[bis(monohalosubstituted phenyl)phosphino]hydrocarbon-bis[chlorogold (I)] complexes represented by the following general structural formula:

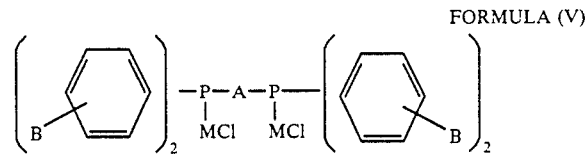

FORMULA (V)

wherein A is as defined above, M is Au(I), and B is halo. The gold complex of Formula (V) is reacted with the appropriate bis[α,ω-di(monohalosubstituted-phenylphosphino)hydrocarbon compound of Formula (VI):

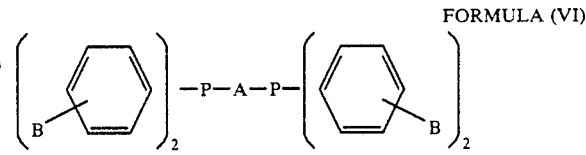

FORMULA (VI)

wherein A and B are as defined above. For example, the dry, powdered derivative of Formula (V) is added to a solution of the appropriate Formula (VI) compound in a nonreactive organic solvent, such as acetone.

The gold complexes of Formula (V) are prepared by reaction of 1 mole equivalent of the appropriate Formula (VI) compound with 2 mole equivalents of a reduced form of chloroauric acid hydrate obtained by treatment with thiodiglycol. The compounds of Formula (VI) are prepared by reacting the appropriate monohalosubstituted phenyl magnesium bromide compound with the appropriate bis(dichlorophosphino)hydrocarbon ligand, which are available from commercial sources, such as Strem Chemicals Inc., Danvers, Mass.

The necessary magnesium bromide compounds can be prepared by methods known to one of skill in the art, for example, by reacting the appropriate monohalosubstituted phenyl compound with magnesium bromide.

Another method which may be utilized by one of skill in the art to prepare gold(I) compounds of Formula (III) is the method of McAuliffe et al., *J.C.S. Dalton*, 1730 (1979), i.e. reacting sodium tetrachloroaurate with the appropriate Formula (IV) or Formula (VI) compound.

Another method which may be utilized by one of skill in the art to prepare gold(I) compounds of Formula (I) is the method of Cariati et al., *Inorg. Chim. Acta*, 1(2), 315-18 (1967), i.e., reacting 1 mole of a solution of hydrogen tetrachloroaurate (chloroauric acid hydrate) in ethanol with two moles of the appropriate Formula (IV) or Formula (VI) compound.

In general, to prepare the gold complexes of Formula (I) where X is other than chloro, either the corresponding Formula (I) products where X is chloro are subject to anion exchange reactions such as by treatment with a salt of the desired X counterion, or the appropriate Formula (III) compound is treated with the appropriate silver salt containing the required anion followed by further reaction with the appropriate Formula (IV) compound. For example, to prepare the gold complexes of Formula (I) where X is nitrate, the corresponding Formula (I) products where X is chloro are treated with, for example, sodium nitrate in acetone solution. Likewise, to prepare the gold complexes of Formula (I) where X is hexafluorophosphate, the corresponding products where X is chloro are treated with, for example, sodium hexafluorophosphate in water solution. As another example, to prepare the gold complexes of Formula (I) wherein X is 2-hydroxypropanoate (lactate), the corresponding compound of Formula (III) wherein X is chloro, is treated with silver lactate in, for example, $CH_2Cl_2$—$CH_3OH$—$H_2O$, followed by further reaction with the appropriate compound of Formula (IV). A more detailed general procedure for the preparation of gold complexes of Formula (I) where X is other than chloro can be found in Example A.

The silver complexes of Formula (I) wherein X is nitrato and R and R' are the same and are phenyl or ethyl, or R is ethyl provided that R' is phenyl, are similarly prepared by reaction of 2 mole equivalents of the appropriate compound of Formula (IV) with 1 mole equivalent of silver nitrate in a nonreactive organic solvent, such as acetone, at room temperature for one-half to one hour.

The silver complexes of Formula (I) wherein X is chloro and R and R' are the same and are monohalosubstituted phenyl are similarly prepared by reacting the appropriate Formula (V) compound wherein M is Ag(I) with the appropriate Formula (VI) compound.

The silver complexes of Formula (V) are prepared by reacting the appropriate Formula (VI) compound with silver (I) nitrate.

In general, to prepare the silver complexes of Formula (I) where X is other than nitrate, the corresponding Formula (I) compound where X is nitrato is treated with a salt of the desired X counterion, preferably an alkali or alkaline earth salt. For example, to prepare the silver complexes of Formula (I) wherein X is chloro, the corresponding Formula (I) products where X is nitrato are treated with, for example, sodium chloride in aqueous acetone solution. Likewise, to prepare the silver complexes of Formula (I) wherein X is hexafluorophosphate, the corresponding products where X is nitrato are treated with, for example, sodium hexafluorophosphate in water solution. A more detailed general procedure for the preparation of silver complexes of Formula (I) where X is other than nitrato can be found in Example B.

In general, to prepare the copper complexes of Formula (I) a copper salt containing the appropriate anion is reacted with the appropriate Formula (IV) or Formula (VI) compound.

The copper complexes of Formula (I) wherein X is chloro and R and R' are the same and are phenyl and A is cis—CH=CH or $(CH_2)_3$, or R and R' are the same and are ethyl or monosubstituted phenyl, or R is ethyl provided that R' is phenyl and A is as defined above are similarly prepared by reacting the appropriate Formula (IV) or Formula (VI) compound with 0.5 mole equivalent of copper(I) chloride.

The copper complex of Formula (II) wherein X is chloro can be prepared by reacting copper(I) chloride with 1,2-bis(diphenylphosphino)ethane, available from commercial sources such as Strem Chemicals, Inc., Danvers, Mass. in chloroform.

To prepare the copper complexes of Formula (I) or Formula (II) where X is nitrate, one of skill in the art may employ the method of Carty et al., *Can J. Chem.*, 49, 761-6, (1971), i.e. reacting an excess of the appropriate Formula (IV) compound with copper (II) nitrate.

To prepare the copper complexes of Formula (I) where X is hexafluorophosphate, the corresponding products where X is chloro are treated with, for example, sodium hexafluorophosphate in water solution.

As stated above, the active ingredients used herein have tumor cell-growth inhibiting activity which has been demonstrated in a variety of test systems.

The B16 melanoma cell assay measures the ability of a compound to inhibit the clonogenic capacity of cells in vitro following a two-hour exposure to the compound. Initially, the cytotoxic activity of the Formula (I) and Formula (II) compounds was evaluated in vitro using B16 melanoma cells according to the following assay:

B16 melanoma (highly metastatic subline, F10) are used and maintained as monolayer cultures in Minimal Essential Media (Grand Island Biological Col., Grand Island, N.Y.) supplemented with 10% calf serum, 1% antibiotics in a 5% $CO_2$ humidified incubator at 37° C. Asynchronous populations of cells are harvested and replated to 5000 cells/plate in sterile 60 mm×15 mm petri plates. Plates are incubated overnight to allow attachment of the cells to the plate. Cells are treated with a Formula (I) or Formula (II) compound/under sterile conditions, allowed to react for 2 hours followed by aspiration of medium. Plates are washed one time with 5 ml of phosphate buffered saline (PBS), followed by the addition of 5 ml of fresh medium. Plates are incubated for 5 days at 37° C. in a $CO_2$ incubator. Viability is measured by the ability of a cell to form a colony of greater than 50 cells. Colonies are fixed with 0.5% crystal violet in 95% ethanol. Plates are dried and counted with a Biotran III Automatic Count Totalizer (New Brunswick Scientific Co., Edison, N.J.). Mean and standard deviation of triplicate samples are determined for each drug concentration. The data are analyzed plotting the log of the survival fraction (number of colonies in drug treated plates/number of colonies in controls) versus the drug concentration.

An evaluation of several compounds of Formula (I) in vitro B16 melanoma assay is shown in Table I.

TABLE I $$\left[\begin{array}{c}(R)_2-P-A-P-(R')_2 \\ \diagdown \quad \diagup \\ M^\oplus \\ \diagup \quad \diagdown \\ (R')_2-P-A-P-(R)_2\end{array}\right]_n X^{n\ominus}$$

| Compound Number | R | R' | A | M | X | n | IC$_{50}$[a] (μM) |
|---|---|---|---|---|---|---|---|
| 1 | phenyl | phenyl | (CH$_2$)$_2$ | Au(I) | Cl | 1 | 4.5 |
| 2 | phenyl | phenyl | (CH$_2$)$_2$ | Ag(I) | NO$_3$ | 1 | 4 |
| 3 | phenyl | phenyl | cis-CH=CH | Au(I) | Cl | 1 | 2 |
| 4 | phenyl | phenyl | (CH$_2$)$_3$ | Au(I) | Cl | 1 | 0.6 |

[a]Concentration which inhibits cloning efficiency of B16 melanoma cells by 50% on a 2-hour exposure Additionally, in another in vitro assay, Compound No. 1 from Table I effectively killed HT-29 human colon carcinoma cells following a 2-hour exposure to concentrations below the 10μM level.

P388 lymphocytic leukemia is an animal tumor model widely used for screening antitumor agents and for detailed evaluation of active compounds. This tumor system is widely accepted as an antitumor agent screening tool because it is sensitive to virtually all of the clinically active antineoplastic agents; quantitative and reproducible; amenable for large-scale screening; and predictive for activity in other animal tumor models. Drugs that are highly active in the intraperitoneal (ip) P388 tumor model are generally active in other tumor models as well. The antitumor activity of the compounds of Formula (I) and Formula (II) is demonstrated in the P388 leukemia mouse model employing the following protocol:

10$^6$ P388 leukemia cells are inoculated ip in B6D2F$_1$ mice. Twenty-four hours later, if the tumor inoculum proves to be free of bacterial contamination (as determined by 24 hours incubation in thioglycollate broth), animals are randomized into groups of 6 and housed in shoebox cages. Metal complexes are dissolved in a minimal volume of either N,N-dimethylacetamide (DMA) or 95% ethanol (depending upon solubility). An equal volume of saline or water is added; if the drug comes out of solution an equal volume of Cremophor (polyethoxylated castor oil) is added and then saline or water, as to a concentration such that the desired dose is delivered in 0.5 ml. The final concentration of DMA, ethanol or Cremophor is 10 percent. Dilutions for lower doses are made with saline or water so that there is a decreasing proportion of organic solvents in the vehicle with decreasing dosage. These vehicles provide soluble formulations (or suspensions). Formulations are prepared immediately prior to injection. The Formula (I) and Formula (II) compounds are administered ip on Days 1 through 5 (i.e., treatment is initiated 24 hrs after tumor inoculation). Each experiment includes three groups of 6 animals as untreated controls and animals treated with a positive control, cisplatin, at two dose levels. Animals are weighed as a group on Days 1, 5 and 9 and average weight change (Δwt.) is used as a reflection of toxicity. Each experiment also includes an inoculum titration—groups of 8 mice inoculated ip with 10$^5$ to 10$^0$ P388 leukemia cells. The titration is used as a quality control check for the performance of the tumor model. Animals are monitored daily for mortality and experiments are terminated after 45 days. The endpoint is median survival time (MST) and increase in lifespan (ILS) which is the percentage of increase in MST relative to untreated controls. Untreated controls inoculated ip with 10$^6$ P388 leukemia cells generally survive for a median of 9 or 11 days. A drug is considered active if it produces ≧25 percent ILS.

a summary of an evaluation of the Formula (I) compounds in the in vivo P388 leukemia model is shown in Table II.

TABLE II

Formula (I)

$$\left[\begin{array}{c}(R)_2-P-A-P-(R')_2 \\ \diagdown \quad \diagup \\ M^\oplus \\ \diagup \quad \diagdown \\ (R')_2-P-A-P-(R)_2\end{array}\right]_n X^{n\ominus}$$

| Compound No. | R | R' | A | X | M | n | MTD[a] (mg/kg) | ILS max[b] (%) |
|---|---|---|---|---|---|---|---|---|
| 1 | phenyl | phenyl | (CH$_2$)$_2$ | Cl | Au(I) | 1 | 2 | 83 ± 24[c] |
| 2 | phenyl | phenyl | (CH$_2$)$_2$ | NO$_3$ | Ag(I) | 1 | 3 | 89/90[d] |
| 3 | phenyl | phenyl | cis-CH=CH | Cl | Au(I) | 1 | 2 | 92 ± 26[e] |
| 4 | phenyl | phenyl | (CH$_2$)$_3$ | Cl | Au(I) | 1 | 3 | 89 ± 28[f] |
| 5 | phenyl | phenyl | (CH$_2$)$_2$ | NO$_3$ | Au(I) | 1 | 3 | 90 ± 17[g] |
| 6 | p-fluoro phenyl | p-fluoro phenyl | (CH$_2$)$_2$ | Cl | Au(I) | 1 | 3 | 55/50 |
| 7 | m-fluoro phenyl | m-fluoro phenyl | (CH$_2$)$_2$ | Cl | Au(I) | 1 | 12 | 45/55 |
| 8 | phenyl | ethyl | (CH$_2$)$_2$ | Cl | Au(I) | 1 | 3 | 54 ± 16[h] |
| 9 | phenyl | ethyl | (CH$_2$)$_2$ | Cl | Cu(I) | 1 | 1.5 | 48/45 |
| 10 | ethyl | ethyl | (CH$_2$)$_2$ | PF$_6$ | Au(I) | 1 | 4 | 40/30 |
| 11 | ethyl | ethyl | (CH$_2$)$_2$ | NO$_3$ | Ag(I) | 1 | 0.5 | 50/40 |
| 12 | phenyl | phenyl | (CH$_2$)$_3$ | Cl | Cu(I) | 1 | 2 | 92 ± 15[i] |
| 13 | phenyl | phenyl | cis-CH=CH | Cl | Cu(I) | 1 | 3 | 70 ± 23[i] |
| 14 | phenyl | phenyl | (CH$_2$)$_2$ | Methane sulfonate | Au(I) | 1 | 2 | 81 ± 17[i] |
| 15 | phenyl | phenyl | (CH$_2$)$_2$ | 2-hydroxy-propanoate | Au(I) | 1 | 2 | 71 ± 12[e] |
| 16 | phenyl | phenyl | (CH$_2$)$_2$ | glucuronate | Au(I) | 1 | 2 | 64 ± 17[i] |

TABLE II-continued

Formula (I)

$$\left[ \begin{array}{c} (R)_2-P-A-P-(R')_2 \\ \diagdown \quad \diagup \\ M^{\oplus} \\ \diagup \quad \diagdown \\ (R')_2-P-A-P-(R)_2 \end{array} \right]_n X^{n\ominus}$$

| Compound No. | R | R' | A | X | M | n | MTD[a] (mg/kg) | ILS max[b] (%) |
|---|---|---|---|---|---|---|---|---|
| 17 | phenyl | phenyl | (CH₂)₂ | sulfate | Au(I) | 2 | 2 | 74/50 |
| 18 | phenyl | phenyl | (CH₂)₂ | cyanate | Au(I) | 1 | 2 | 84/50 |
| 19 | phenyl | phenyl | (CH₂)₂ | citrate | Au(I) | 3 | 4 | 95/90 |
| 20 | phenyl | phenyl | (CH₂)₂ | trifluoro-methane sulfonate | Au(I) | 1 | 2 | 63/75 |
| 21 | phenyl | phenyl | (CH₂)₂ | 2-oxopropanoate | Au(I) | 1 | 2 | 60/50 |
| 22 | phenyl | phenyl | (CH₂)₂ | 4-hydroxy-butanoate | Au(I) | 1 | 2 | 65/70 |
| 23 | phenyl | phenyl | (CH₂)₂ | hydroxy-acetate | Au(I) | 1 | 2 | 55/75 |
| 24 | phenyl | phenyl | (CH₂)₂ | 2-hydroxy-butanoate | Au(I) | 1 | 2 | 55/80 |
| 25 | phenyl | phenyl | (CH₂)₂ | 2,3-dihydroxy-propanoate | Au(I) | 1 | 2 | 55/65 |
| 26 | phenyl | phenyl | (CH₂)₂ | 2-hydroxy-ethyl sulfonate | Au(I) | 1 | 2 | 55/78 |

[a] maximally tolerated dose for B6D2F female mice on an ip qDX5 regimen.
[b] maximum increase in lifespan produced in mice bearing ip P388 leukemia.
[c] data based on 33 different experiments.
[d] figures separated by slashes represent data generated in separate experiments.
[e] data based on 7 different experiments.
[f] data based on 3 different experiments.
[g] data based on 5 different experiments.
[h] data based on 4 different experiments.

Additionally, the Formula (II) compound wherein X is chloro was tested twice in the ip P388 leukemia model and exhibited an ILS of 100% and 115% at a MTD of 2 mg/kg.

Based on the data set forth in Tables I and II, the compounds of Formula (I) and Formula (II) showed significant cytotoxicity and antitumor activity. In particular, the compound of Formula (I) wherein R and R' are phenyl, A is (CH₂)₂, M is Au(I) and X is Cl is preferred due to its activity in the P388 leukemia mouse assay with an ILS.

Another tumor model used for evaluation of tumor growth inhibiting drugs is intraperitoneally implanted M5076 reticulum cell sarcoma in mice. In this system B6D2F, female mice are inoculated with 0.5 ml of a 10 percent (w:v) brei of M5076 prepared from Pooled sc tumors excised at about 21 days from C57Bl/6 donors. Drugs are administered ip. Daily treatment is begun 24 hours after implantation and is continued for ten days. The treatment regimen for M5076 is more prolonged than for P388 because of the slower growth rate and longer control survival time of the M5076 tumor. Compounds of Formula (I) and Formula (II) were evaluated in this assay. An evaluation of several compounds of Formula (I) in the M5076 reticulum cell sarcoma assay at their maximally tolerated dose (MTD) is set forth in Table III. An ILS of ≧25% indicates activity in this tumor model.

TABLE III

| Compound No.[a] | MTD (mg/kg)[b] | ILS (max)[c] % |
|---|---|---|
| 1 | 2 | 56/83/52/47/49 |
| 2 | 2 | 48 |
| 3 | 2.4 | 69 |
| 4 | 2 | 116 |
| 8 | 2 | 46 |

TABLE III-continued

| Compound No.[a] | MTD (mg/kg)[b] | ILS (max)[c] % |
|---|---|---|
| 13 | 2 | 40 |

[a] see Table II for structures
[b] maximally tolerated dose for B6D2F female mice on an ip qDX10 regimen
[c] maximum increase in lifespan produced in mice bearing ip M5076 reticulum cell sarcoma (figures separated by slashes were generated in separate experiments)

Additionally, the Formula (II) compound wherein X is chloro was tested in the M5076 reticulum cell sarcoma assay and exhibited an ILS of 60% at a MTD of 1.6 mg/kg.

The cytotoxic activity of several Formula (I) and Formula (II) compounds was evaluated in vivo using B16 melanoma cells. In this system, groups of eight B6D2F₁ mice are inoculated ip with 0.5 ml of a 10% (w:v) brei of B16 melanoma prepared from pooled sc tumors excised at 14-21 days from C67B₁/6 donor mice. Daily treatment is begun 24 hours after tumor implantation and is continued daily for ten (10) days. The route of drug administration is ip. The mice are monitored daily for survival for sixty (60) days. Antitumor activity is assessed by prolongation of median survival time. An ILS of ≧25% indicates activity in this tumor model.

A summary of the results of the in vivo ip B16 melanoma assay is shown in Table IV.

TABLE IV

| Compound No.[a] | MTD (mg/kg)[b] | ILS (%)[c] |
|---|---|---|
| 1 | 2 | 50/43/33/28/37 |
| 4 | 2 | 34/28/40 |
| 3 | 1.5 | 35 |
| 13 | 0.75 | 42 |
| 12 | 1 | 32/47 |
| 15 | 1.5 | 30 |
| 16 | 1.5 | 40 |

TABLE IV-continued

| Compound No.[a] | MTD (mg/kg)[b] | ILS (%)[c] |
|---|---|---|
| 25 | 0.75 | 28 |

[a]see Table A for structure
[b]maximally tolerated dose for B6D2F$_1$ mice on an ip qDX10 regimen
[c]maximum increase in lifespan produced in mice bearing ip B16 melanoma (figures separated by a slash were generated in separate experiments).

Additionally, the Formula (II) compound wherein X is chloro was tested in the ip B16 melanoma assay and exhibited an ILS of 54% at a MTD of 1 mg/kg. Compound No. 1 from Table II was also tested in a further in vivo tumor model, mammary adenocarcinoma 16/c, a tumor model sensitive to DNA binders and alkylating agents. In this experiment, the tumor was implanted sc in C3H mice, and the drug was administered ip or iv on an intermittent treatment schedule, i.e., once on days 1, 5, 9, 13 and 17. Tumors were measured 3 weeks after implantation, and activity was assessed by degree of tumor growth inhibition. Cisplatin, a drug which generally produces complete inhibition of the growth of mammary adenocarcinoma 16/c, was used as a positive control. A tumor growth inhibition of $\geq 75\%$ indicates that a drug is active in this type of animal tumor model. The results of this assay are summarized in Table V.

TABLE V

| Drug | Regimen | | Mean Tumor Volume (mm³) on Day 21 | Inhibition (%) | N.P.* |
|---|---|---|---|---|---|
| | Route and Schedule of Administration | Optimal Dose (mg/kg) | | | |
| *Experiment 1* | | | | | |
| Control | | | 1187 ± 999 | | 1/24 |
| Cisplatin | ip, q4D × 5 | 6 | 30 ± 64 | 97 | 6/8 |
| Compound No. 1[a] | ip, q4D × 5 | 8 | 96 ± 143 | 92 | 4/7 |
| *Experiment 2* | | | | | |
| Control | | | 1113 ± 626 | | 0/23 |
| Cisplatin | ip, q4D × 5 | 6 | 0 | 100 | 8/8 |
| | iv, q4D × 5 | 6 | 21 ± 61 | 98 | 7/8 |
| Compound No. 1 | ip, q4D × 5 | 6 | 430 ± 291 | 61 | 0/8 |
| | iv, q4D × 5 | 12 | 181 ± 163 | 84 | 2/8 |
| *Experiment 3* | | | | | |
| Control | | | 936 ± 353 | | 0/24 |
| Cisplatin | ip, q4D × 5 | 6 | 586 ± 266 | 37 | 0/8 |
| Compound No. 1 | ip, q4D × 5 | 8 | 0. | 100 | 5/5 |

*N.P. = Proportion of mice without palpable tumors on Day 21
[a]See Table II for structure Additionally, Compound No. 1 from Table II was tested in another in vivo tumor model known as subcutaneous M5076 reticulum cell sarcoma in mice according to the following protocol:

B6D2F female mice are inoculated sc in the flank with 0.5 ml of a 10% (w:v) brei of M5076 prepared from pooled sc tumors excised at about Day 21 from C57Bl/6 donors. Treatment is initiated one day after tumor implantation, and is continued daily for 10 days. Tumors are measured 21 days after tumor implantation activity is determined by the degree of tumor growth inhibition. Generally, $\geq 75\%$ inhibition of tumor growth reflects significant antitumor effect. Cisplatin, the positive control compound, produces complete tumor growth inhibition. The results of this assay are summarized in Table VI.

TABLE VI

| Dose (mg/kg) | Dosage regimen | Tumor Growth Inhibition (Day 21) | | | Control MTV[c] |
|---|---|---|---|---|---|
| | | N.P.[a] | MTV[b] | % Inhibition | |
| 2 | ip, qD × 10 | 2/7 | 61 ± 39 | 91 | 661 ± 385 |
| 2 | ip, qD × 10 | 1/7 | 168 ± 112 | 48 | 356 ± 323 |

[a]N.P. = Proportion of mice without palpable tumor on Day 21.
[b]MTV = Mean Tumor Volume (mm³) ± s.d. on Day 21.
[c]MTV = Mean Tumor Volume (mm³) ± s.d. on Day 21.

The pharmaceutical compositions of this invention comprise an effective tumor cell growth-inhibiting amount of a compound of Formula (I) or Formula (II), and an inert pharmaceutically acceptable carrier or diluent. These compositions are prepared in dosage unit form appropriate for parenteral administration.

Compositions according to the invention for parenteral administration include sterile aqueous or non-aqueous solutions, suspensions or emulsions. The composition may be in the form of a solution of the active ingredient in a minimal volume of dimethylacetamide or ethanol, for example 5% v/v, brought up to volume with peanut oil or normal saline solution. Polyethoxylated castor oil, for example 2 to 5% v/v, may also be used to solubilize the active ingredient. In addition, the composition may be in the form of a slurry with, for example, hydroxypropyl cellulose or other suitable suspending agent. As an emulsifying agent, lecithin for example may be used. The composition may also be provided in the form of a sterile solid which can be dissolved in a sterile injectable medium immediately before use.

Freireich et al., Cancer Chemo. Rept., 50, 219–244 (1966), compared the quantitative toxicity of 18 anticancer drugs in six species after correcting the data to a uniform schedule of treatment for five consecutive days. This analysis demonstrated that mouse, rat, dog, human, monkey and man have essentially the same maximum tolerated dose (MTD) when compared on a basis of mg/m² of body surface area. The study suggested that Phase I clinical trials could be safely initiated at a dose one-third the animal MTD. The mouse was as useful as any other species in this regard on which to base the calculation. The appropriate therapeutically effective dose for any compound of the invention can therefore be determined readily by those skilled in the art from simple experimentation with laboratory animals, preferably mice.

It will be appreciated that the actual preferred dosages of the compounds of Formula (I) or Formula (II) used in the compositions of this invention will vary according to the particular complex being used, the particular composition formulated, the mode of administration and the particular site, host and disease being treated. The route of internal administration should be selected to ensure that an effective tumor cell growth inhibiting-amount of the metal complex contacts the tumor. Optimal dosages for a given set of conditions can be ascertained by those skilled in the art using conventional dosage determination tests in view of the above experimental data. For parenteral administration the dose generally employed is from about 1 mg to about 40 mg/m² of body surface per day for five days, repeated about every fourth week for four courses of treatment.

The method for inhibiting the growth of tumor cells sensitive to a compound of Formula (I) or Formula (II) in accordance with this invention comprises administering to a host animal afflicted with said tumor cells, an effective tumor cell growth-inhibiting amount of a compound of Formula (I) or Formula (II). The effective tumor cell growth-inhibiting amount of a compound of Formula (I) or Formula (II) used in the compositions of this invention will vary according to the particular complex being used, the particular composition formulated, the mode of administration and the particular site, host and disease being treated.

The method for inhibiting the growth of tumor cells sensitive to a compound of Formula (I) or Formula (II) in accordance with this invention comprises administering to a host animal afflicted with said tumor cells, an effective tumor cell growth-inhibiting amount of a compound of Formula (I) or Formula (II).

Due to the incapability of Compound No. 1 of Table II to be soluble in water (i.e., it forms a suspension in water), and its ability to form a true solution in a 9:1 water:ethanol solution, various counterion analogs of Compound No. I were examined for their solubility in a 9:1 water:ethanol solution to determine which of such counterion analogs would be more readily soluble in a pharmaceutical composition comprising 9:1 water:ethanol solution as the carrier or diluent. Such solubility was determined as follows: The compound in question was dissolved or suspended in absolute ethanol (250 mg solid per 1.0 ml ethanol). To the resulting solution or suspension, water (9.0 times the volume of ethanol) was added. This suspension was stirred vigorously for 15 hours, then filtered through a 0.45 μm poly(tetrafluoroethylene) (PTFE) filter. The concentration of the filtrate was determined by comparison of high pressure liquid chromatography (HPLC) peak areas with standard solutions of Bis[1,2-bis(diphenylphosphine)ethane]gold(I) 2-hydroxypropanoate in 9:1 water:ethanol. The HPLC system was as follows:

1. Column PLRP-S, 5μm, obtained from Polymer Laboratories, Inc.
2. Mobile Phase 9:1 acetonitrile:0.1% tetra-n-butylammonium hydrogen sulfate (50° C., 1.0 ml-min.$^{-1}$)
3. Detection Ultraviolet (250 nm)

The results obtained are listed in Table VII.

TABLE VII

| Compound No. (a) | Solubility in 9:1 Water:Ethanol (mg-ml$^{-1}$) |
|---|---|
| 1 | 0.17 |
| 5 | 0.03 |
| 14 | 0.03 |
| 15 | 5.2 |
| 16 | 0.30 |
| 17 | 0.03 |
| 18 | 0.06 |
| 19 | 0.03 |
| 20 | 0.02 |
| 21 | 0.20 |
| 22 | 2.9 |
| 23 | 8.6 |
| 24 | 0.9 |
| 25 | 2.2 |
| 26 | 0.03 |

(a) see Table II for structure

As can be clearly seen from Table VII, the ability of a counterion analog of Compound No. I of Table II to be more or less soluble in a 9:1 water: ethanol solution is totally unpredictable because no single physical property of the counterion (e.g., size, lipophilicity, charge) correlates with the observed solubilities. The ability of a counterion analog of Compound No. I of Table II to be more soluble than Compound No. I in a 9:1 water:ethanol solution is very advantageous because it enables such counterion analog to be formulated into a simpler and less toxic formulation, i.e., smaller quantities of the formulation need to be administered since the more soluble such counterion analog of Compound No. 1 is in a 9:1 water ethanol solution, the greater the amount of such analog which can be solubilized by the solution.

Compounds of Formula (I) or Formula (II) (particularly those which are less soluble than Compound No. 1 of Table II in a 9:1 water:ethanol solution) can also be formulated into a microemulsion according to the following protocol: Add 6 ml of ethanol to approximately 200 mg (more or less depending on solubility in ethanol) of a compound of Formula (I) or Formula (II) to form a solution. Disperse 4.8 g of egg lecithin in 9 ml of water, Mix the above by slowly adding the lecithin dispersion to the alcoholic solution while sonicating the mixture. When the addition is completed, add water sufficient to a total of 90 ml while continuing to sonicate. Add 40 ml of soybean oil/cholesterol solution, (200 mg cholesterol/10 ml soybean oil), and homogenize to form a coarse dispersion. Sonicate the dispersion for 30 minutes to produce the microemulsion.

EXAMPLES

The following examples illustrate the chemical preparation of several compounds of Formula (I) and Formula (II) used in the compositions and methods of this invention and as such are not to be construed as limiting the scope thereof. All temperatures are in degrees Centigrade.

EXAMPLE 1

Bis[1,2-Bis(diphenylphosphino)ethane]Gold(I) Chloride

Method A

Sodium chloroaurate hydrate (0.45 g, 1.1 mmol) was reduced to gold(I) by thiodiglycol (0.28 g, 2.2 mmol) in 7 ml of 2.5:1 aqueous acetone. When the solution became colorless 1,2-bis(diphenylphosphino)ethane (0.22 g, 0.55 mmol), obtained from Strem Chemicals, Inc., Danvers, Mass., in 10 ml of acetone was added dropwise over 5 minutes. After stirring for one hour, the white solid [1,2-bis(diphenylphosphino)ethane]bis-[chlorogold(I)] was filtered off, washed with water and then acetone, yield 95%, melting point (m.p.) 262°–267°.

[1,2-bis(diphenylphosphino)ethane]bis[chlorogold(I)] (0.89 g, 1.025 mmol), prepared as described above, was added as a solid to a solution of 1,2-bis(diphenylphosphino)ethane (1.35 g, 3.38 mmol), obtained from Strem Chemicals, Inc., Danvers, Mass., in about 25 ml of acetone. The resultant clear solution was stirred for one hour and crystals were obtained by cooling overnight at 3°. A second crop of product was obtained by concentrating the solvent at room temperature, total yield 70%, m.p. 155°–270°.

Method B

Sodium chloroaurate hydrate (0.5 g, 1.35 mmol) was reduced by thiodiglycol (0.33 g, 2.70 mmol) in aqueous acetone (2.5:1, 7 ml). The solution was cooled to 0°–5° and added dropwise with stirring to a solution of 1,2-bis(diphenylphosphino)ethane (1.07 g, 2.70 mmol), obtained from Strem Chemicals, Inc., Danvers, Mass., in about 30 ml of acetone. A clear colorless solution resulted which was stirred for 30 minutes and then the solvent was concentrated to 10 ml at room temperature. The solid product was obtained by addition of water, was recrystallized from aqueous methanol, washed with cold aqueous methanol and dried in vacuo, yield 79%, m.p. between 173°–277° in 3 stages.

EXAMPLE 2

Bis[1,3-Bis(diphenylphosphino)propane]Gold(I) Chloride

Sodium chloroaurate (2 mol eq) was reduced in situ by thiodiglycol (4 mol eq) in 3:1 aqueous acetone and 1,3-bis(diphenylphosphino)propane (1 mol eq), obtained from Strem Chemicals, Inc., Danvers, Mass., in a minimum volume of acetone was added dropwise to give an immediate white precipitate, [1,3-bis(diphenylphosphino) propane]bis[chlorogold(I)]. This was filtered, washed with water, then ether and dried in vacuo, yield 77%, m.p 245°–255°.

Solid [1,3-bis(diphenylphosphino)propane]bis [chlorogold(I)] (140 mg, 0.16 mmol), prepared as described above, was added to a stirred solution of 1,3-bis (diphenylphosphino)propane (198 mg, 0.48 mmol), obtained from Strem Chemicals, Inc., Danvers, Mass., in 5 ml of acetone. The solid completely dissolved and a white crystalline solid immediately separated from the solution. This was filtered and washed with cold acetone and ether. A second crop was obtained by adding water to the cloud point, total yield 70%, m.p. 193°–195°.

EXAMPLE

Bis[1,2-bis(diphenylphosphino)ethane]Gold(I) Nitrate

Solid [1,2-bis(diphenylphosphino)ethane]bis [chlorogold(I)] (0.40 g, 0.46 mmol), prepared as described in Example 1, was added to a solution of bis(1,2-diphenylphosphino)ethane (0.55 g, 1.39 mmol), obtained from Strem Chemicals, Inc., Danvers, Mass., in 25 ml of acetone. The resultant clear solution was stirred for 30 minutes and then sodium nitrate (0.40 g, 4.6 mmol) in 10 ml of water was added. The product was obtained as a white crystalline solid by slow evaporation of the solvent at room temperature, and was washed with water and dried in vacuo, m.p. 190°–200°.

EXAMPLE 4

Bis[cis-1,2-bis(diphenylphosphino)ethylene]Gold(I) Chloride

Sodium chloroaurate hydrate (0.5 g, 1.35 mmol) was reduced by thiodiglycol (0.33 g, 2.70 mmol) in 7 ml of 2.5:1 aqueous acetone giving a clear colorless solution. The cooled solution was added with stirring to a solution of cis-bis(1,2-diphenylphosphino)ethylene (1.07 g, 2.7 mmol), obtained from Strem Chemicals, Inc., Danvers, Mass., in 25 ml of acetone. The product crystallized from solution after reducing the volume to 10 ml, was filtered, washed thoroughly with water and then dried in vacuo, yield 88%, m.p. 226°–250°.

EXAMPLE 5

Bis[1,2-bis(diphenylphosphino)ethane]Silver(I) Nitrate

Silver nitrate (0.10 g, 0.60 mmol) in 1 ml of water was added to a solution of 1,2-bis(diphenylphosphino) ethane (0.50 g, 1.25 mmol), obtained from Strem Chemicals, Inc., Danvers, Mass., in 25 ml of acetone. The clear solution was stirred for 30 minutes, the volume reduced to about 10 ml and the product precipitated by the addition of about 50 ml of water. White needles were obtained by recrystallization from acetone/water, washed with water and dried in vacuo, yield 90%, m.p. 225°–230°.

EXAMPLE 6

Bis[1,2-bis(diethylphosphino)ethane]Silver(I) Nitrate

Solid silver nitrate (0.21 g, 1.22 mmol) was added to a solution of 1,2-bis(diethylphosphino)ethane (0.51 g (0.55 ml), 2.45 mmol), obtained from Strem Chemicals, Inc., Danvers, Mass., in $CHCl_3$ (5 ml). The crystals all dissolved after a few minutes, and the clear solution was stirred for 30 minutes. The solvent was evaporated at room temperature, leaving a clear oil, then the complex was isolated as a white powder by repeated scratching in ice-cold $Et_2O$ and hexane and was dried in vacuo, yield 70%, m.p. 104°–114°.

EXAMPLE 7

Bis[1,2-bis(diethylphosphino)ethane]Gold(I) Hexafluorophosphate

Solid [1,2-bis(diethylphosphino)ethane]bis[chlorogold(I)], (0.53 g, 0.79 mmol) prepared as described in Example 1, was suspended in acetone (10 ml) and 1,2-bis(diethylphosphino)ethane (0.54 g (0.58 ml), 2.61 mmol), obtained from Strem Chemicals, Inc., Danvers, Mass., was added dropwise. After stirring for a few minutes, a clear solution was obtained. This was stirred for 30 minutes, and then $NaPF_6$ (0.27 g, 1.58 mmol) in $H_2O$ (3 ml) was added dropwise. The volume was reduced to 5 ml, and the complex obtained as a white solid after the addition of $H_2O$ (25 ml), and recrystallization from EtOH, yield 83%, m.p. 240°–255°.

EXAMPLE 8

Bis[1-diethylphosphino-2-diphenylphosphino)ethane]-Copper(I) Chloride

Solid copper(I) chloride (0.081 g, 0.81 mmol) was added to a fresh solution of (1-diethylphosphino-2-diphenylphosphino)ethane (0.54 g (0.50 ml), 1.79 mmol), obtained from Strem Chemicals, Inc., Danvers, Mass., in $CHCl_3$ (10 ml) in an $N_2$ atmosphere. After stirring under a steady stream of $N_2$ for 2 hours, all the solid had dissolved, hexane (10 ml) was added, and the solution was left at 3° for 24 hours. The solvent was decanted from the clear oily residue, and the product was obtained as a white solid after scratching the oil in ice cold acetone (1 ml) and ice cold hexane (1 ml), yield 0.42 g, m.p. 112°–115°.

EXAMPLE 9

Bis[1-diethylphosphino-2-diphenylphosphino)ethane]Gold(I) Chloride

Solid [bis(1-diethylphosphino-2-diphenylphosphino)ethane] bis[chlorogold(I)] (0.26 g, (0.34 mmol) [prepared with (1-diethylphosphino-2-diphenylphosphino) ethane substantially in accordance with the procedure described in Example 1] was added to a solution of (1-diethylphosphino-2-diphenylphosphino)ethane (0.34 g, (0.31 ml) 1.12 mmol) obtained from Strem Chemicals, Inc., Danvers, Mass., in CHCl$_3$ (10 ml) giving a clear colorless solution. This was stirred for 30 minutes, and then the solvent was evaporated to dryness at room temperature giving a clear gum. The product was obtained as a white solid by scratching the gum in ice-cold Et$_2$O, yield 90%, m.p. 170°–200°.

EXAMPLE 10

Tris[1,2-bis(diphenylphosphino)ethane]Dicopper(I) Chloride

Copper (I) chloride (0.087 g, 0.88 mmol) was added as a solid to a solution of [1,2-bis(diphenylphosphino)ethane] (0.88 g, 2.2 mmol), obtained from Strem Chemicals, Inc., Danvers, Mass., in chloroform (10 ml). After stirring for two hours under a steady stream of N$_2$, all the solid had dissolved. The product was obtained as a white precipitate, by the addition of hexane (5 ml), on cooling to 3°, and was filtered and dried in vacuo; yield 50%, m.p. 260°–270°.

EXAMPLE 11

Bis[1,2-bis[bis(4-fluorophenyl)phosphino]ethane Gold(I) Chloride

Thiodiglycol, 2.1 g (0.017 mol) was added to a stirred solution of 2.47 g (0.006 mol) of chloroauric acid in a mixture of 10 ml water and 30 ml CH$_3$OH. When a colorless solution resulted, 1.30 g (2.276 mmol) 1,2-ethanediyl-bis[bis (4-fluorophenyl)phosphine, [prepared by reacting 1,2-bis(dichlorophosphino)ethane, obtained from Strem Chemicals Inc., Danvers, Mass., with a Grignard reagent of 4-fluorophenyl magnesium bromide in THF] in a mixture of 30 ml CHCl$_3$—30 ml CH$_3$OH was added dropwise with cooling. After the addition was complete, the reaction mixture was stirred an additional 30 minutes. The product (separated solid) was removed, dried and yielded 2.55 g of μ-[1,2-bis[(4-fluorophenyl) phosphino]ethane]bis[chlorogold(I)] with a melting point of 271°–272°.

Dry, powdered μ-[1,2-bis[(4-fluorophenyl) phosphino]ethane]bis[chlorogold(I)](0.561 g, 0.6 mmol), prepared as described above, was stirred into a solution containing 0.847 g (1.8 mmol) of -bis[bis(4-fluorophenyl/phosphine], prepared as described above, in 15 ml of acetone. The resulting was filtered and the filtrate concentrated under reduced pressure to an amorphous solid. Crystallization of the solid from MeOH/H$_2$O gave 0.91 g of the named product, m.p. 229°–230°.

EXAMPLE 12

Bis[1,2-bis[bis(. Phosphino]ethane]Gold(I) Chloride

A solution containing 2.73 g (5.8 mmol) of 1,2-ethanediyl-bis[bis(3-fluorophenyl)phosphine], prepared using 3-fluorophenyl magnesium substantially in accordance with the procedure outlined in Example 12, in 25 ml of acetone was stirred into ice-cooled solution of gold (I), prepared by adding 0.87 ml (8.7 mmol) of thiodiglycol to a mixture of 5 mL H$_2$O/20 ml CH$_3$OH containing 1.196 g (2.9 mmol) of chloroauric acid tetrahydrate. The semisolid residue that separated on refrigeration overnight was solidified by trituration under ether. Recrystallization from CH$_2$Cl$_2$/toluene gave 1.267 g of named product, m.p. 235°–245°.

EXAMPLE 13

Bis[1,3-bis(diphenylphosphino)propane]Copper(I) Chloride

Copper(I) chloride (0.132 g, 1.33 mmol) was added as a solid to a solution of 1,3-bis 1phosphino)propane (1.108 g, 2.68 mmol), obtained from Strem Chemicals Inc., Danvers, Mass., in chloroform (ca 50 ml.). After stirring for 1 hour under a steady stream of N$_2$, the solid had dissolved, giving a yellow solution. The solvent was removed by rotary evaporation, and the oily residue was solidified by repeated trituration in ice-cold hexane (1 ml) and ice-cold diethylether (1 ml). The product was recrystallized from MeOH (3 ml) by the addition of H$_2$O (10 ml), and was dried in vacuo; yield 60%, m.p. 90°–115°.

EXAMPLE 14

Bis[cis-1,2-bis(diphenylphosphino)ethylene]Copper(I) Chloride

Copper(I) chloride (0.078 g, 0.79 mmol) was added as a solid to a solution of [cis-1,2 bis(diphenylphosphino)ethylene] (0.66 g, 1.66 mmol), obtained from Strem Chemicals Inc., Danvers, Mass., in chloroform (ca 25ml). After stirring for 1 hour under a steady stream of N$_2$, all the solid dissolved, giving a yellow solution. The volume was reduced to 5 ml by rotary evaporation, and white crystals formed on cooling to 0°. These were filtered and recrystallized from MeOH (5 ml) after the addition of H$_2$O (20 ml), and were dried in vacuo, yield 70%, m.p. 169°–178°.

EXAMPLE 15

Tris[1,2-bis(diphenylphosphino)ethane]dicopper(I) Nitrate

The named product can be prepared by the method of Carty et al., Can J. Chem., 49, 761–766 (1971), according to the following procedure: copper(II) nitrate is reduced by excess 1,2-bis(diphenylphosphino)ethane in hot ethanol, and then n-hexane is added which yields colorless crystals of the named product, m.p. 131°–135°.

EXAMPLE 16

Bis[1,2-bis(diphenylphosphino)ethane]copper(I) Nitrate

The named product can be prepared by the method of Carty et al., Can J. Chem., 49, 761–766 (1971), according to the following procedure: the named product can be isolated from solutions of product of Example 16 by bubbling oxygen through a refluxing ethanolic solution for 3 hours. Large crystals of the named product can be obtained on slow evaporation, m.p. 213°–215°.

EXAMPLE 17

Bis[1,2-bis(diphenylphosphino)ethane]gold(I) Bromide

The named product was prepared by the method outlined in Example 1, Method B, except that 4 equivalents of sodium bromide were mixed with sodium chloroaurate hydrate in the initial water (5 ml). The named product was obtained in 73% yield, m.p. 182°–188°.

EXAMPLE 18

Bis[1,2-bis(diphenylphosphino)ethane]gold(I) Iodide

The named product was prepared by the method outlined in Example 1, Method B, except that a fourfold excess of sodium iodide (in 1 ml $H_2O$) with respect to gold was added to the solution of bis[1,2-bis(diphenylphosphino)ethane]gold (I) chloride in situ before addition of $H_2O$ to precipitate the named iodide complex, m.p. 165°–170°.

EXAMPLE 19

Bis[1,2-bis(diphenylphosphino)ethane]gold(I) methanesulfonate

Solid bis[1,2-bis(diphenylphosphino)ethane]gold(I) chloride hereinafter referred to as "[Au(dppe)$_2$]Cl", (1.0 g, 0.97 mmol), prepared as described in Example 1, was dissolved in 50 ml of a 3:1 ethanol:water solution. A solution of silver methane sulfonate (0.19 g, 0.94 mmol) in 30 ml of 3:1 ethanol:water was added to the first solution. After stirring the mixture, shielded from light, for 24 hours, it was filtered through diatomaceous earth. Ethanol was removed by rotary evaporation, causing the product to precipitate as a white solid. The solid was filtered, washed with 50 ml of water, and dried under vacuum, yield 0.67 g (63%), m.p. 195°–200°.

EXAMPLE 20

Bis[1,2-bis(diphenylphosphino)ethane]gold(I) 2-hydroxypropanoate

Solid [1,2-bis(diphenylphosphino)ethane]bis [chlorogold(I)], hereinafter referred to as "(AuCl)$_2$dppe", (0.50 g, 0.58 mmol), prepared as described in Example 1, was dissolved in 20 ml of degassed methylene chloride ($CH_2Cl_2$), then 15 ml degassed $CH_3OH$ was added. A solution of silver DL-2-hydroxypropanoate (0.23 g, 1.17 mmol) in 30 ml of 1:1 $CH_3OH:H_2O$ (degassed) was added to the first solution. After stirring the mixture for 5 hours, shielded from light, it was filtered through diatomaceous earth. 1,2-Bis(diphenylphosphino)ethane (0.69 g, 1.73 mmol) was added to the filtrate and the solution was stirred for 60 minutes. The solution was then filtered and rotary evaporated to dryness. The residue was stirred with 50 ml of $CH_2Cl_2$ and 25 ml of water. The organic layer was recovered and the aqueous layer was washed with 25 ml of $CH_2Cl_2$. The combined organic layers were dried over $MgSO_4$, filtered, and rotary evaporated to an oil. The product was further dried under vacuum to a flocculent, off-white solid, yield 1.13 g (65%), m.p. 84°–90°.

EXAMPLE 21

Bis[1,2-bis(diphenylphosphino)ethane]gold(I) glucuronate (AuCl)$_2$dppe (0.50 g, 0.58 mmol), prepared as described in Example 1, was dissolved in 20 ml of degassed $CH_2Cl_2$, then 15 ml of degassed $CH_3OH$ added. A solution of silver DL-glucuronate (0.35 g, 1.16 mmol) in 30 ml of 1:1 $CH_3OH:H_2O$ (degassed) was added to the first solution. After stirring the mixture, shielded from light, for 15 hours, it was filtered through diatomaceous earth. 1,2-Bis(diphenylphosphino)ethane (0.69 g, 1.73 mmol) was added to the filtrate and the resulting solution stirred for 60 minutes. The solution was then filtered and rotary evaporated to dryness. The residue was extracted from 25 ml of water into 50 ml of $CH_2Cl_2$. The organic layer was recovered and the aqueous layer was washed with 25 ml of $CH_2Cl_2$. The combined organic layers were dried over $MgSO_4$, filtered, and rotary evaporated to an oil. The product was further dried under vacuum to a flocculent, off-white solid, yield 0.79 g (57%), m.p. 111°–114°.

EXAMPLE 22

Bis[1,2-bis(diphenylphosphino)ethane]gold(I) cyanate a. Silver cyanate (AgOCN was prepared as follows:

Sodium cyanate, NaOCN, (1.91 g, 29 mmol), obtained from Aldrich Chemicals, Milwaukee, Wis., was dissolved in 75 ml of water. A solution of silver nitrate, $AgNO_3$, (5.0 g, 29 mmol) in 40 ml of water was added, producing a white precipitate. The solid was filtered, washed with water, and under vacuum.

b. Bis[1,2-bis(diphenylphosphino)ethane]gold(I) cyanate.

[Au(dppe)$_2$]Cl (1.0 g, 1 0 mmol), prepared as described in Example 1, was in 60 ml of 1:1 $CH_3CN:H_2O$. As a solid, AgOCN (0.14 g, 0.93 mmol), prepared as described above, was added, and the mixture was stirred, protected from light, for 3 days. The suspension was filtered through diatomaceous earth. Acetonitrile was removed from the filtrate by rotary evaporation, producing a white suspension. The solid was recovered by filtration, washed with water, and dried under vacuum for several hours, m.p. 188°–191°.

EXAMPLE 23

Bis{bis[1,2-bis(diphenylphosphino)ethane]gold(I)} sulfate

[Au(dppe)$_2$]Cl (1.0 g, 1.0 mmol), prepared as described in Example 1, was dissolved in 25 ml of 1:1 $CH_3CN:H_2O$. A solution of silver sulfate, $Ag_2SO_4$ (0.14 g, 0.69 mmol), obtained from Pfaltz and Bauer, Inc., Waterbury, Conn., in a small amount of 1:1 $CH_3CN:H_2O$ was added to the first solution. The mixture was stirred, protected from light, for 36 hours, then filtered through diatomaceous earth and a 0.5 μm filter. Acetonitrile was removed by rotary evaporation, causing the product to precipitate from solution as an off-white powder. This powder was recovered by filtration, then redissolved in $CH_3CH/H_2O$, filtered, and recovered as before by rotary evaporation. The off-white solid was filtered, washed with water, and dried under vacuum for several hours, m.p. 150°–154°.

EXAMPLE 24

Tris{bis-[1,2-bis(diphenylphosphino)ethane]gold(I)} citrate

[Au(dppe)$_2$]Cl (3.0 g, 2.9 mmol), prepared as described in Example 1, was dissolved in 150 ml of 1:1 $CH_3CN:H_2O$. Silver citrate, $Ag_3[O_2CC(OH)(CH_2CO_2)_2]$, (0.49 g, 0.96 mmol), obtained from Pfaltz & Bauer, Inc., Waterbury, Conn., was added as a solid. The reaction was stirred, protected from light, for 3 days. The mixture was filtered through diatomaceous earth. The filtrate was rotary evaporated to remove the acetonitrile, causing a white solid to precipitate. The solid was filtered, washed with water, and dried under vacuum for several hours, yield 2.00 g (65%), m.p. 177°–185°.

EXAMPLE 25

Bis[1,2-bis(diphenylphosphino)ethane]gold(I) trifluoromethanesulfonate

[Au(dppe)$_2$]Cl (1.0 g, 1.0 mmol), prepared as described in Example 1, was dissolved in 50 ml of 1:1 CH$_3$CN:H$_2$O. A solution of silver trifluoromethane sulfonate, AgOSO$_2$CF$_3$ (0.25 g, 1.0 mmol), obtained from Pfaltz and Bauer, Inc., Waterbury, Conn., in 20 ml of 1:1 CH$_3$CN:H$_2$O was added, and the resulting mixture was stirred for 15 hours, protected from light. The suspension was filtered through diatomaceous earth. Acetonitrile was removed from the filtrate by rotary evaporation, producing a white solid. The solid was filtered, washed with water, and dried for several hours under vacuum, yield 0.53 g (48%), m.p. 240°–246°.

EXAMPLE 26

Bis[1,2-bis(diphenylphosphino)ethane]gold(I) 2-oxopropanoate a. Silver 2-oxopropanoate (AgOC(O)C(O)CH$_3$)

Sodium 2-oxopropanoate (5.0 gm, 45 mmol) obtained from Pfaltz and Bauer, Inc., Waterbury, Conn., was dissolved in 100 ml of water. A solution of AgNO$_3$ (7.7 g 45 mmol) in 50 ml of water was added and the mixture was stirred for ½ hour. 150 ml of MeOH were added and the mixture was cooled to 0° C. A white precipitate formed and was filtered, washed with H$_2$O/ MeOH (1:1) and dried under vacuum, yield 5.90 g (67%).

b. Bis[1,2-bis(diphenylphosphino)ethane]gold(I) 2-oxopropanoate (AuCl)$_2$dppe (0.50 g, 0.58 mmol), prepared as described in Example 1, was dissolved in 20 ml of degassed CH$_2$Cl$_2$, and 15 ml of degassed MeOH were added. A slurry of silver 2-oxopropanoate (0.23 g, 1.18 mmol), prepared as described above, 30 ml of 1:1 MeOH/H$_2$O was added to the above solution. The mixture was shielded from light and stirred overnight. The purple solid was filtered off through diatomaceous earth. 1,2 bis-(diphenylphosphino)ethane, hereinafter referred to as "dppe", (0.69 g, 1.73 mmol) was added to the filtrate and the mixture was stirred for 1 hour. The insolubles were filtered off and the solution was rotary evaporated to dryness. The crude product was dissolved in 60 ml of CH$_2$Cl$_2$ and 15 ml of H$_2$O were added. The CH$_2$C$_2$ layer was separated and the aqueous phase was washed with 20 ml of CH$_2$Cl$_2$. The organic phases were combined, dried with MgSO$_4$, filtered and rotary evaporated to dryness. The product was dried under vacuum overnight, yield 0.90 g (72%), m.p. 61°–64°.

EXAMPLE 27

Bis[1,2-(diphenylphosphino)ethane]gold(I) 4-hydroxybutanoate a. Silver 4-hydroxybutanoate (AgOC(O) (CH$_2$)$_3$OH)

Sodium 4-hydroxybutanoate (2.5 g, 19.8 mmol), obtained from Aldrich Chemicals, Milwaukee, Wis., was dissolved in 50 ml of water. A solution of AgNO$_3$ (3.37 g, 19.8 mmol) in 25 ml of water was added and the mixture was stirred for ½ hour. 75 ml of MeOH were added and the mixture was cooled to 0°. A precipitate formed and was filtered, washed with H$_2$O/MeOH (1:1) and dried under vacuum, yield 2.16 g (52%).

b. Bis[1,2-(diphenylphosphino)ethane]gold(I)4-hydroxybutanoate (AuCl)$_2$dppe (0.50 g, 0.58 mmol), prepared as described in Example 1, was dissolved in 20 ml of degassed CH$_2$Cl$_2$ and 15 ml of degassed MeOH were added. A slurry of silver 4-hydroxybutanoate (0.25 g, 1.18 mmol), prepared as described above, in 30 ml of 1:1 MeOH/H$_2$O was added to the above solution. The mixture was shielded from light and stirred overnight. The precipitate was filtered off through diatomaceous earth. Dppe (0.69 g, 1.73 mmol) was added to the filtrate and the mixture was stirred for 1 hour. The solution was filtered and rotary evaporated to dryness. The crude product was dissolved in 60 ml of CH$_2$Cl$_2$ and 15 ml of H$_2$O were added. The CH$_2$Cl$_2$ layer was separated and the aqueous phase was washed with 20 ml of CH$_2$Cl$_2$. The organic phases were combined, dried with MgSO$_4$, filtered, and rotary evaporated to dryness. The product was dried under vacuum, yield 0.85 g (67%), m.p. 60°–63°.

EXAMPLE 28

Bis[1,2-bis(diphenylphosphino)ethane]gold(I) hydroxyacetate

A. Silver hydroxyacetate (AgOC(O)CH$_2$OH)

Calcium hydroxyacetate 2.0 g, 10.5 mmol), obtained from Pfaltz and Bauer, Waterbury, Conn., was dissolved in 200 ml of water. A solution of AgNO$_3$ (3.58 g, 21.0 mmol) in 30 ml of water was added and the mixture was stirred for ½hour. 100 ml of MeOH were added and the mixture was cooled to 0° C. White crystals formed and were filtered, washed with cold H$_2$O/MeOH (1:1) and dried under vacuum, yield 0.67 g (17%).

b. Bis[1,2-bis(diphenylphosphino)ethane]gold(I) hydroxyacetate (AuCl)$_2$dppe (0.50 g, 0.58 mmol), prepared as described in Example 1, was dissolved in 20 ml of degassed CH$_2$Cl$_2$ and 15 ml of MeOH were added. A slurry of silver hydroxyacetate (0.21 g, 1.18 mmol), prepared as described in part a, in 30 ml of 1:1 MeOH/H$_2$O was added to the above solution. The mixture was shielded from light and stirred overnight. The precipitate was filtered off through diatomaceous earth. Dppe (0.69 g, 1.73 mmol) was added to the filtrate and the mixture was stirred for 1 hour. The solution was filtered and rotary evaporated to dryness. The crude product was dissolved in 60 ml of CH$_2$Cl$_2$ and 20 of water were added. The organic layer was separated and the aqueous phase was washed with 20 ml of CH$_2$Cl$_2$. The organic phases were combined, dried with MgSO$_4$, filtered, and rotary evaporated to dryness. The product was dried under vacuum, yield 0.95 g (77%), m.p. 60°–70°.

EXAMPLE 29

Bis[1,2-bis(diphenylphosphino)ethane]gold(I) DL-2-hydroxybutanoate a. Silver DL-2-hydroxybutanoate (AgOC(O)CH(OH)CH$_2$CH$_3$)

Sodium DL-2-hydroxybutanoate (1.0 g, 7.9 mmol), obtained from Aldrich Chemicals, Milwaukee, Wis., was dissolved in 20 ml of water. A solution of AgNO$_3$ (1.35 g, 7.9 mmol) in 10 of water were added and the mixture was stirred for ½ hour. 30 ml of acetone were added and the mixture was cooled to 0° C. A white precipitate formed and was filtered, washed with acetone/water (1:1) and dried under vacuum, yield 0.74 g (44%).

Bis[1,2-bis(diphenylphosphino)ethane]gold(I) DL-2-hydroxybutanoate $(AuCl)_2$dppe (0.50 g, 0.58 mmol), prepared as described in Example 1, was dissolved in 20 ml of degassed $CH_2Cl_2$ and 30 ml of MeOH and 15 ml of water were added. Silver DL-2-hydroxybutanoate (0.24 g, 1.16 mmol), prepared as described above, was added and the reaction was shielded from light and stirred overnight. The precipitate was filtered off diatomaceous earth. 1,2-bis(diphenylphosphino)ethane (dppe) (0.69 g, 1.73 mmol) was added to the filtrate and the mixture was stirred for 1 hour. The solution was filtered and rotary evaporated to dryness. The crude product was dissolved in 60 ml of $CH_2Cl_2$ and 15 ml of water added. The organic layer was separated and the aqueous phase was washed with 20 ml of $CH_2Cl_2$. The organic phases were combined, dried with $MgSO_4$, filtered, and rotary evaporated to dryness. The product was dried under vacuum, yield 0.97 g (76%), m.p. 73°–75°.

EXAMPLE 30

Bis[1,2-bis(diphenylphosphino)ethane]gold(I) DL-2,3-dihydroxypropanoate a. Silver DL-2,3-dihydroxypropanoate (AgOC(O)CH(OH) $CH_2OH$)

Calcium DL-2,3-dihydroxypropanoate (0.50 g, 1.75 mmol), obtained from Aldrich Chemicals, Milwaukee, Wis., was dissolved in 20 ml of water. A solution of sodium carbonate (0.19 g, 1.75 mmol) in 10 ml of water was added and an immediate precipitate formed. The solid was filtered off and silver nitrate (0.5 g, 3.5 mmol) was added to the filtrate. The mixture stirred for 15 minutes. 75 ml of MeOH were added and the mixture was cooled to 0°. A white precipitate formed and was filtered, washed with MeOH/$H_2O$ (1:1 and dried under vacuum, yield 0.43 g (58%).

b. Bis[1,2-bis(diphenylphosphino)ethane]gold(I) DL-2,3-dihydroxypropanoate $(AuCl)_2$dppe (0.50 g, 0.58 mmol), prepared as described in Example 1, was dissolved in 20 ml of degassed $CH_2Cl_2$ and 30 ml of MeOH and 15 ml of water were added. Silver DL-2,3-dihydroxypropanoate (0.25 g, 1.16 mmol), prepared as described above, was added and the reaction was shielded from light and stirred overnight. The precipitate was filtered off through diatomaceous earth. Dppe (0.69 g, 1.73 mmol) was added to the filtrate and the mixture was stirred for 3 hours. The solution was filtered and rotary evaporated to dryness. The crude product was dissolved in 60 ml of $CH_2Cl_2$ and 15 ml of water were added. The organic layer was separated and the aqueous phase was washed with 20 ml of $CH_2Cl_2$. The organic phases were combined, dried the $MgSO_4$, filtered and rotary evaporated to dryness. The product was dried under vacuum, yield 0.93 g (73%), m.p. 71°–74°.

EXAMPLE 31

Bis[1,2-bis(diphenylphosphino)ethane]Silver (I) Acetate

Solid silver acetate (0.125 g, 0.75 mmol) was added to a solution of 1,2-bis(diphenylphosphino)ethane (0.597 g, 1.50 mmol) obtained from Strem Chemicals Inc., Danvers, Mass., in $CHCl_3$ (10 ml). The solid dissolved after stirring for 30 minutes. Then hexane was added to the cloud point. The gum isolated after decanting off the solvent was solidified by scratching in ice-cold ether and was dried in vacuo, yield 67%, m.p. 212°–223°.

EXAMPLE 32

As a specific embodiment of a pharmaceutical composition of this invention, an active ingredient, such as one part of the complex of Example 1, is dissolved in 5 parts of dimethylacetamide and 5 parts of polyethoxylated castor oil and then normal saline solution qs, and is administered parenterally in one dose of 5 mg/m² per day for 5 days to inhibit the growth of tumor cells sensitive to the active ingredient in an animal afflicted by such tumor cells.

EXAMPLE A

General Procedure for the Preparation of Gold Complexes of Formula (I) where X is other than Chloro The appropriate gold compound of Formula (III) where X is chloro, prepared, for example, by the method of Example 1, is dissolved in an approximate 1:1 mixture of dichloromethane and methanol (each degassed). One equivalent per gold of a salt of the desired counterion, such as the silver salt, is added to this solution under an inert atmosphere. The mixture stirred, protected from light, for 15–20 hours. After filtering through diatomaceous earth, the solution is stirred with 1.5 equivalents per gold of the appropriate compound of Formula (IV) or (VI) (solid) per gold for 1–3 hours. This solution is then filtered and dried to a solid. The residue is extracted from water with dichloromethane, dried with magnesium sulfate, and the solvent is removed under reduced pressure.

EXAMPLE B

General Procedure for the Preparation of Silver Complexes of Formula (I) where X is other than Nitrato One equivalent of the silver salt containing the desired counterion is added to a solution containing 2 equivalents of the appropriate compound of Formula (IV) or (VI) in, for example, chloroform. The mixture is stirred under an inert atmosphere and protected from light for ½–3 hours or until the salt has dissolved. The product is precipitated with, for example, hexane, and is filtered and dried under vacuum.

EXAMPLE C

General Procedure for the Preparation of Copper Complexes of Formula (I) where X is other than chloro.

The copper salt containing the appropriate counterion is added to a solution containing at least 2 equivalents of the appropriate Formula (IV) or Formula (VI) compound in, for example, chloroform. This mixture is stirred in an inert atmosphere for 1–3 hours or until the salt has dissolved. The product is precipitated with, for example, hexane and is filtered and dried under vacuum.

What is claimed is:

1. A pharmaceutical composition which comprises an effective tumor cell growth-inhibiting amount of an active ingredient and an inert pharmaceutically acceptable carrier or diluent, wherein said active ingredient is a compound of Formula (I) or Formula (II):

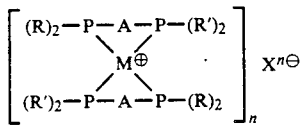

Formula (I)

wherein
R and R' are the same and are phenyl, ethyl or monosubstituted phenyl wherein said substituent is halo, or R' is ethyl when R is phenyl;
A is the same and is $(CH_2)_m$ or cis—CH=CH;
m is 2 or 3;
X is a pharmaceutically acceptable counterion;
n is equal to the negative charge of the counterion; and
M is Au(I), Ag(I) or Cu(I); provided that
(a) when M is Cu(I), R and R' are the same and are phenyl, and A is $(CH_2)_2$, X is other than halo;
(b) when R and R' are the same and are ethyl, A is $(CH_2)_2$ and M is Au(I), X is other than halo;

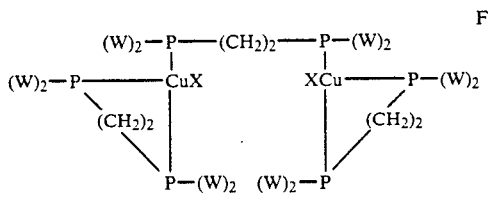

Formula (II)

wherein
W is the same and is phenyl; and
X is the same and is halo or nitrato.

2. The composition of claim 1 in which the composition is in dosage unit form adapted for parenteral administration.

3. The composition of claim 2 in which the parenteral dosage unit is adapted to administer 1 mg to about 40 mg/m² of body surface.

4. The composition of claim 1 wherein the active ingredient is a compound of Formula (I).

5. The composition of claim 4 wherein R' is ethyl when R is phenyl, A is $(CH_2)_2$, M is Au(I), X is chloro, and n is 1.

6. The composition of claim 4 wherein R and R' are the same and are phenyl, A is $(CH_2)_2$, M is Ag(I), X is chloro, and n is 1.

7. The composition of claim 4 wherein R' and R are the same and are phenyl, A is $(CH_2)_2$, M is Ag(I), X is nitrato, and n is 1.

8. The composition of claim 4 wherein R and R' are the same and are phenyl, A is cis—CH=CH, M is Au(I), X is chloro, and n is 1.

9. The composition of claim 4 wherein R and R' are the same and are phenyl, A is $(CH_2)_3$, M is Au(I), X is chloro, and n is 1.

10. The composition of claim 4 wherein R and R' are the same and are phenyl, A is $(CH_2)_2$, M is Au(I), X is methanesulfonate, and n is 1.

11. The composition of claim 4 wherein R and R' are the same and are phenyl, A is $(CH_2)_2$, M is Au(I), X is 2-hydroxypropanoate, and n is 1.

12. The composition of claim 4 wherein R and R' are the same and are phenyl, A is $(CH_2)_2$, M is Au(I), X is glucuronate, and n is 1.

13. The composition of claim 4 wherein R and R' are the same and are phenyl, A is $(CH_2)_2$, M is Au(I), X is sulfate, and n is 2.

14. The composition of claim 4 wherein R and R' are the same and are phenyl, A is $(CH_2)_2$, M is Au(I), X is cyanate, and n is 1.

15. The composition of claim 4 wherein R and R' are the same and are phenyl, A is $(CH_2)_2$, M is Au(I), X is trifluoromethane sulfonate, and n is 1.

16. The composition of claim 4 wherein R and R' are the same and are phenyl, A is $(CH_2)_2$, M is Au(I), X is 2-oxopropanoate, and n is 1.

17. The composition of claim 4 wherein R and R' are the same and are phenyl, A is $(CH_2)_2$, M is Au(I), X is 4-hydroxybutanoate, and n is 1.

18. The composition of claim 4 wherein R and R' are the same and are phenyl, A is $(CH_2)_2$, M is Au(I), X is hydroxyacetate, and n is 1.

19. The composition of claim 4 wherein R and R' are the same and are phenyl, A is $(CH_2)_2$, M is Au(I), X is 2-hydroxybutanoate, and n is 1.

20. The composition of claim 4 wherein R and R' are the same and are phenyl, A is $(CH_2)_2$, M is Au(I), X is 2,3-dihydroxypropanoate, and n is 1.

21. The composition of claim 4 wherein R and R' are the same and are phenyl, A is $(CH_2)_2$, M is Au(I), X is 2-hydroxyethylsulfonate, and n is 1.

22. The composition of claim 1 wherein the active ingredient is a compound of Formula (II) and X is the same and is chloro.

23. A method for inhibiting growth of tumor cells which comprises administering internally to an animal afflicted by said tumor cells an effective tumor cell growth-inhibiting amount of a compound of Formula (I) or Formula (II):

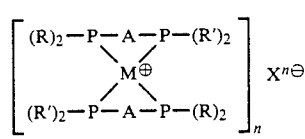

Formula (I)

wherein
R and R' are the same and are phenyl, ethyl or monosubstituted phenyl wherein said substituent is halo, or R' is ethyl when R is phenyl;
A is the same and is $(CH_2)_m$ or cis—CH=CH;
m is 2 or 3;
X is a pharmaceutically acceptable counterion;
n is equal to the negative charge of the counterion; and
M is Au(I), Ag(I) or Cu(I); provided that
(a) when M is Cu(I), R and R' are the same and are phenyl, and A is $(CH_2)_2$, X is other than halo; and
(b) when R and R' are the same and are ethyl, A is $(CH_2)_2$ and M is Au(I), X is other than halo;

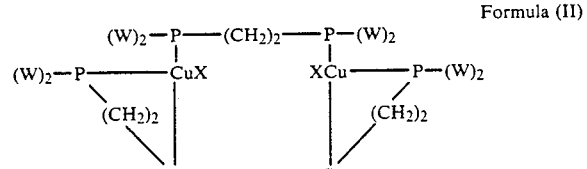

Formula (II)

wherein

W is the same and is phenyl; and

X is the same and is halo or nitrato.

24. The method of claim 23 in which the administration is parenteral and the amount is selected from the unit dose range of from about 1 mg to about 40 mg/m² of body surface administered per day for five days.

25. The method of claim 24 in which the administration is repeated about every fourth week for four courses of treatment.

26. The method of claim 23 wherein the compound is a compound of Formula (I).

27. The method of claim 27 wherein R' is ethyl when R is phenyl, A is (CH₂)₂, M is Ag(I), X is chloro, and n is 1.

28. The method of claim 27 wherein R and R' are the same and are phenyl, A is (CH₂)₂, M is Au(I), X is chloro, and n is 1.

29. The method of claim 27 wherein R' and R are the same and are phenyl, A is (CH₂)₂, M is Ag(I), X is nitrato, and n is 1.

30. The method of claim 27 wherein R' and R are the same and are phenyl, A is cis—CH=CH, M is Au(I), X is chloro, and n is 1.

31. The method of claim 27 wherein R' and R are the same and are phenyl, A is (CH₂)₃, M is Au(I), X is chloro, and n is 1.

32. The method of claim 23 wherein R and R' are the same and are phenyl, A is (CH₂)₂, M is Au(I), X is methanesulfonate, and n is 1.

33. The method of claim 23 wherein R and R' are the same and are phenyl, A is (CH₂)₂, M is Au(I), X is 2-hydroxypropanoate, and n is 1.

34. The method of claim 27 wherein R and R' are the same and are phenyl, A is (CH₂)₂, M is Au(I), X is glucuronate, and n is 1.

35. The method of claim 27 wherein R and R' are the same and are phenyl, A is (CH₂)₂, M is Au(I), X is sulfate, and n is 2.

36. The method of claim 27 wherein R and R' are the same and are phenyl, A is (CH₂)₂, M is Au(I), X is cyanate, and n is 1.

37. The method of claim 27 wherein R and R' are the same and are phenyl, A is (CH₂)₂, M is Au(I), X is trifluoromethane sulfonate, and n is 1.

38. The method of claim 27 wherein R and R' are the same and are phenyl, A is (CH₂)₂, M is Au(I), X is 2-oxopropanoate, and n is 1.

39. The method of claim 27 wherein R and R' are the same and are phenyl, A is (CH₂)₂, M is Au(I), X is 4-hydroxybutanoate, and n is 1.

40. The method of claim 27 wherein R and R' are the same and are phenyl, A is (CH₂)₂, M is Au(I), X is hydroxyacetate, and n is 1.

41. The method of claim 27 wherein R and R' are the same and are phenyl, A is (CH₂)₂, M is Au(I), X is 2-hydroxybutanoate, and n is 1.

42. The method of claim 27 wherein R and R' are the same and are phenyl, A is (CH₂)₂, M is Au(I), X is 2,3-dihydroxypropanoate, and n is 1.

43. The method of claim 27 wherein R and R' are the same and are phenyl, A is (CH₂)₂, M is Au(I), X is 2-hydroxyethyl sulfonate, and n is 1.

44. The method of claim 23 wherein the compound is compound of Formula (II) and X is the same and is chloro.

45. A method for treating tumor cells sensitive to bis[1,2-bis(diphenylphosphino)ethane]gold(I) chloride in a host animal afflicted with such tumor cells which comprises parenterally administering to the host animal a solution or suspension containing an effective tumor cell growth-inhibiting amount of bis[1,2-bis(diphenylphosphino)ethane]gold(I) chloride.

46. A method of treating tumor cells sensitive to bis[1,2-bis(diphenylphosphino)ethane]gold(I) 2-hydroxypropanoate in a host animal afflicted with such tumor cells which comprises parenterally administering to the host animal a solution of suspension containing an effective tumor cell growth-inhibitor amount of bis[1,2-bis(diphenylphosphino)ethane]gold(I) 2-hydroxypropanoate.

47. A compound of the formula:

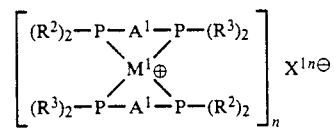

wherein

R² and R³ are the same and are phenyl, ethyl or monosubstituted phenyl wherein said substitutent is halo, or R² is ethyl when R³ is phenyl;

A¹ is the same and is (CH₂)$_m$ or cis—CH=CH;

m is 2 or 3;

X¹ is a pharmaceutically acceptable counterion;

n is equal to the negative charge of the counterion; and

M¹ is Au(I) or Cu(I); provided that:

(a) when M¹ is Cu(I), R² and R³ are the same and are phenyl, and A¹ is (CH₂)₂, X¹ is other than halo or nitrato;

(b) when R² and R³ are the same and are ethyl, A¹ is (CH₂)₂ and M¹ is Au(I), X¹ is other than halo; and (c) when R² and R³ are the same and are phenyl, A¹ is (CH₂)₂ and M¹ is Au(I), X¹ is other than chloro, hexafluoroantimonate-acetone or thiocyanate.

48. The compound of claim 47 wherein R² and R³ are the same and R² is ethyl when R³ is phenyl, A¹ is the same and is (CH₂)₂, (CH₃)₃ or cis—CH=CH, M¹ is Au(I) or Ag(I) and X¹ is chloro or nitrato; provided that when A¹ is (CH₂)₂ and M¹ is Au(I), X¹ is other than chloro.

49. The compound of claim 47 wherein R² is ethyl when R³ is phenyl, A is (CH₂)₂, M¹ is Au(I), X¹ is chloro, and n is 1.

50. The compound of claim 47 wherein R² and R³ are the same and are phenyl, A¹ is (CH₂)₂, M¹ is Au(I), X is nitrato, and n is 1.

51. The compound of claim 47 wherein R² and R³ are the same and are phenyl, A¹ is (CH²)₂, M¹ is Ag(I), X¹ is nitrato, and n is 1.

52. The compound of claim 47 wherein R² and R³ are the same and are phenyl, A¹ is cis—CH=CH, M¹ is Au(I), X¹ is chloro, and n is 1.

53. The compound of claim 47 wherein R² and R³ are the same and are phenyl, A¹ is (CH₂)₃, M¹ is Au(I), X¹ is chloro, and n is 1.

54. The compound of claim 47 wherein R and R' are the same and are phenyl, A is (CH₂)₂, M is Au(I), X is methanesulfonate, and n is 1.

55. The compound of claim 47 wherein R and R' are the same and are phenyl, A is (CH₂)₂, M is Au(I), X is 2-hydroxypropanoate, and n is 1.

56. The compound of claim 47 wherein R and R' are the same and are phenyl, A is (CH$_2$)$_2$, M is Au(I), X is glucuronate, and n is 1.

57. The compound of claim 47 wherein R and R' are the same and are phenyl, A is (CH$_2$)$_2$, M is Au(I), X is sulfate, and n is 2.

58. The compound of claim 47 wherein R and R' are the same and are phenyl, A is (CH$_2$)$_2$, M is Au(I), X is cyanate, and n is 1.

59. The compound of claim 47 wherein R and R' are the same and are phenyl, A, is (CH$_2$)$_2$, M is Au(I), X is trifluoromethanesulffonate, and n is 1.

60. The compound of claim 47 wherein R and R' are the same and are phenyl, A is (CH$_2$)$_2$, M is Au(I), X is 2-oxopropanoate, and n is 1.

61. The compound of claim 47 wherein R and R' are the same and are phenyl, A is (CH$_2$)$_2$, M is Au(I), X is 4-hydroxybutanoate, and n is 1.

62. The compound of claim 47 wherein R and R' are the same and are phenyl, A is (CH$_2$)$_2$, M is Au(I), X is hydroxyacetate, and n is 1.

63. The compound of claim 47 wherein R and R' are the same and are phenyl, A is (CH$_2$)$_2$, M is Au(I), X is 2-hydroxybutanoate, and n is 1.

64. The compound of claim 47 wherein R and R' are the same and are phenyl, A is (CH$_2$)$_2$, M is Au(I), X is 2,3-dihydroxypropanoate, and n is 1.

65. The compound of claim 47 wherein R and R' are the same and are phenyl, A is (CH$_2$)$_2$, M is Au(I), X is 2-hydroxyethyl sulfonate, and n is 1.

* * * * *